US008419720B1

(12) United States Patent  
Dawoodjee

(10) Patent No.: US 8,419,720 B1  
(45) Date of Patent: Apr. 16, 2013

(54) FLEXIBLE LAPAROSCOPIC DEVICE

(75) Inventor: Aziz E. Dawoodjee, Canoga Park, CA (US)

(73) Assignee: National Advanced Endoscopy Devices, Incorporated, Canoga Park, CA (US)

( * ) Notice: Subject to any disclaimer, the term of this patent is extended or adjusted under 35 U.S.C. 154(b) by 1 day.

(21) Appl. No.: 13/367,852

(22) Filed: Feb. 7, 2012

(51) Int. Cl.
*A61B 17/00* (2006.01)

(52) U.S. Cl.
USPC ............................... 606/1; 600/104; 600/136

(58) Field of Classification Search .......................... None
See application file for complete search history.

(56) References Cited

U.S. PATENT DOCUMENTS

| | | | |
|---|---|---|---|
| 1,915,811 A | 6/1933 | Wolf | |
| 2,424,064 A | 7/1947 | Stegeman | |
| 2,975,785 A | 3/1961 | Sheldon | |
| 3,012,463 A | 12/1961 | Krivit | |
| 3,060,972 A | 10/1962 | Sheldon | |
| 3,071,161 A | 1/1963 | Ulrich | |
| 3,162,214 A | 12/1964 | Bazinet, Jr | |
| 3,190,286 A | 6/1965 | Stokes | |
| 3,266,059 A | 8/1966 | Stelle | |
| 3,270,641 A | 9/1966 | Gosselin | |
| 3,525,331 A | 8/1970 | Mori | |
| 3,557,780 A | 1/1971 | Sato | |
| 3,572,325 A | 3/1971 | Bazell et al. | |
| 3,583,393 A | 6/1971 | Takahashi | |
| 3,788,304 A | 1/1974 | Takahashi | |
| 3,799,151 A | 3/1974 | Fukaumi et al. | |
| 3,892,228 A | 7/1975 | Mitsui | |
| 3,913,568 A | 10/1975 | Carpenter | |
| 4,108,211 A | 8/1978 | Tanaka | |
| 4,271,845 A | 6/1981 | Chikashige et al. | |
| 4,290,421 A | 9/1981 | Siegmund | |
| 4,351,323 A | 9/1982 | Ouchi et al. | |
| 4,432,349 A | 2/1984 | Oshiro | |
| 4,483,326 A | 11/1984 | Yamaka et al. | |
| 4,530,568 A | 7/1985 | Haduch et al. | |
| 4,593,682 A | 6/1986 | Heckele | |
| 4,651,718 A | 3/1987 | Collins et al. | |
| 4,669,172 A | 6/1987 | Petruzzi | |
| 4,686,963 A | 8/1987 | Cohen et al. | |

(Continued)

FOREIGN PATENT DOCUMENTS

| | | |
|---|---|---|
| EP | 0906061 | 9/2004 |
| EP | 1604607 | 10/2006 |

(Continued)

*Primary Examiner* — Bill Thomson  
*Assistant Examiner* — Lynsey Crandall  
(74) *Attorney, Agent, or Firm* — Tutunjian & Bitetto, P.C.

(57) ABSTRACT

A laparoscopic device that includes an outer rod having a end connected to a handle and an end having an articulated section formed from links joined with non-diametrical hinges; an actuation rod within the outer rod, having an end connected to the handle and an end connected to a tension element within the articulated section, configured to cause the articulated section to bend when tension is applied; and an attachment rod within the actuation rod having an end connected to the handle and an end having a flexible section connected to a tool. The handle includes an actuator configured to apply tension to the attachment rod such that the tool is activated; a rod actuator configured to apply tension to the actuation rod such that the articulated section of the outer rod bends; and a lockable rotator, configured to rotate the outer rod with respect to the handle.

16 Claims, 5 Drawing Sheets

U.S. PATENT DOCUMENTS

| | | | |
|---|---|---|---|
| 4,688,554 A | 8/1987 | Habib | |
| 4,700,693 A | 10/1987 | Lia et al. | |
| 4,714,075 A | 12/1987 | Krauter et al. | |
| 4,726,355 A | 2/1988 | Okada | |
| 4,758,222 A | 7/1988 | McCoy | |
| 4,762,118 A | 8/1988 | Lia et al. | |
| 4,773,395 A | 9/1988 | Suzuki et al. | |
| 4,779,612 A | 10/1988 | Kishi | |
| 4,790,294 A | 12/1988 | Allred, III et al. | |
| 4,796,607 A | 1/1989 | Allred, III et al. | |
| 4,805,596 A | 2/1989 | Hatori | |
| 4,834,069 A | 5/1989 | Umeda | |
| 4,836,189 A | 6/1989 | Allred, III et al. | |
| 4,841,951 A | 6/1989 | Umeda | |
| 4,841,952 A | 6/1989 | Sato et al. | |
| 4,846,573 A | 7/1989 | Taylor et al. | |
| 4,881,810 A | 11/1989 | Hasegawa | |
| 4,895,431 A | 1/1990 | Tsujiuchi et al. | |
| 4,904,048 A | 2/1990 | Sogawa et al. | |
| 4,934,340 A | 6/1990 | Ebling et al. | |
| 4,947,827 A | 8/1990 | Opie et al. | |
| 5,005,558 A | 4/1991 | Aomori | |
| 5,018,509 A | 5/1991 | Suzuki et al. | |
| 5,105,819 A | 4/1992 | Wollschlager et al. | |
| 5,114,402 A | 5/1992 | McCoy | |
| 5,174,276 A | 12/1992 | Crockard | |
| 5,174,277 A | 12/1992 | Matsumaru | |
| 5,178,129 A | 1/1993 | Chikama et al. | |
| 5,197,457 A | 3/1993 | Adair | |
| 5,220,911 A | 6/1993 | Tamura | |
| 5,231,989 A | 8/1993 | Middleman et al. | |
| 5,251,611 A | 10/1993 | Zehel et al. | |
| 5,254,130 A | 10/1993 | Poncet et al. | |
| 5,261,905 A * | 11/1993 | Doresey, III | 606/45 |
| 5,271,381 A | 12/1993 | Ailinger et al. | |
| 5,271,382 A | 12/1993 | Chikama | |
| 5,295,477 A | 3/1994 | Janfaza | |
| 5,318,586 A | 6/1994 | Ereren | |
| 5,345,937 A | 9/1994 | Middleman et al. | |
| 5,400,773 A | 3/1995 | Zhu et al. | |
| 5,417,203 A | 5/1995 | Tovey et al. | |
| 5,448,989 A | 9/1995 | Heckele | |
| 5,474,057 A | 12/1995 | Makower et al. | |
| 5,522,788 A | 6/1996 | Kuzmak | |
| 5,558,665 A | 9/1996 | Kieturakis | |
| 5,618,294 A | 4/1997 | Aust et al. | |
| 5,620,415 A * | 4/1997 | Lucey et al. | 604/22 |
| 5,624,380 A | 4/1997 | Takayamna et al. | |
| 5,643,294 A | 7/1997 | Tovey et al. | |
| 5,645,520 A | 7/1997 | Nakamura et al. | |
| 5,656,011 A | 8/1997 | Uihlein et al. | |
| 5,681,263 A | 10/1997 | Flesch | |
| 5,683,348 A | 11/1997 | Diener | |
| 5,683,349 A | 11/1997 | Makower et al. | |
| 5,728,121 A | 3/1998 | Bimbo et al. | |
| 5,749,828 A | 5/1998 | Solomon et al. | |
| 5,772,578 A | 6/1998 | Heimberger et al. | |
| 5,776,114 A | 7/1998 | Frantzen et al. | |
| 5,785,647 A | 7/1998 | Tompkins et al. | |
| 5,787,897 A | 8/1998 | Kieturakis | |
| 5,807,241 A | 9/1998 | Heimberger | |
| 5,810,716 A | 9/1998 | Mukherjee et al. | |
| 5,857,964 A | 1/1999 | Konstorum et al. | |
| 5,860,914 A | 1/1999 | Chiba et al. | |
| 5,873,817 A | 2/1999 | Kokish et al. | |
| 5,885,258 A | 3/1999 | Sachdeva et al. | |
| 5,897,488 A | 4/1999 | Ueda | |
| 5,928,136 A | 7/1999 | Barry | |
| 5,938,588 A | 8/1999 | Grabover et al. | |
| 5,976,076 A | 11/1999 | Kolff et al. | |
| 6,077,287 A | 6/2000 | Taylor et al. | |
| 6,162,171 A | 12/2000 | Ng et al. | |
| 6,171,316 B1 | 1/2001 | Kovac et al. | |
| 6,190,399 B1 | 2/2001 | Palmer et al. | |
| 6,270,453 B1 | 8/2001 | Sakai | |
| 6,302,841 B1 | 10/2001 | Hatori et al. | |
| 6,364,828 B1 | 4/2002 | Yeung et al. | |
| 6,408,889 B1 | 6/2002 | Komachi | |
| 6,443,944 B1 | 9/2002 | Doshi et al. | |
| 6,450,950 B2 | 9/2002 | Irion | |
| 6,475,140 B1 | 11/2002 | Konstorum et al. | |
| 6,482,149 B1 | 11/2002 | Torii | |
| 6,491,626 B1 | 12/2002 | Stone et al. | |
| 6,641,528 B2 | 11/2003 | Torii | |
| 6,663,641 B1 | 12/2003 | Kovac et al. | |
| 6,743,239 B1 | 6/2004 | Kuehn et al. | |
| 6,749,560 B1 | 6/2004 | Konstorum et al. | |
| 6,761,685 B2 | 7/2004 | Adams et al. | |
| 6,780,151 B2 | 8/2004 | Grabover et al. | |
| 6,790,173 B2 | 9/2004 | Saadat et al. | |
| 6,858,005 B2 | 2/2005 | Ohline et al. | |
| 6,899,672 B2 | 5/2005 | Chin et al. | |
| 6,991,603 B2 | 1/2006 | Krupa et al. | |
| 7,008,375 B2 | 3/2006 | Weisel | |
| 7,044,906 B2 | 5/2006 | Hosoi et al. | |
| 7,090,637 B2 | 8/2006 | Danitz et al. | |
| 7,101,334 B2 | 9/2006 | Takahashi | |
| 7,250,027 B2 | 7/2007 | Barry | |
| 7,320,700 B2 | 1/2008 | Cooper et al. | |
| 7,326,176 B2 | 2/2008 | Machiya et al. | |
| 7,410,483 B2 | 8/2008 | Danitz et al. | |
| 7,553,275 B2 | 6/2009 | Padget et al. | |
| 7,591,783 B2 | 9/2009 | Boulais et al. | |
| 7,608,083 B2 | 10/2009 | Lee et al. | |
| 7,637,905 B2 | 12/2009 | Saadat et al. | |
| 7,670,284 B2 | 3/2010 | Padget et al. | |
| 7,682,307 B2 | 3/2010 | Danitz et al. | |
| 7,682,319 B2 | 3/2010 | Martin et al. | |
| 7,766,821 B2 | 8/2010 | Brunnen et al. | |
| 7,779,845 B2 | 8/2010 | Ortiz | |
| 7,785,252 B2 | 8/2010 | Danitz et al. | |
| 7,828,724 B2 | 11/2010 | Hosoi et al. | |
| 7,833,154 B2 | 11/2010 | Aono et al. | |
| 7,837,620 B2 | 11/2010 | Nobis et al. | |
| 7,842,028 B2 | 11/2010 | Lee | |
| 7,862,580 B2 | 1/2011 | Cooper et al. | |
| 7,874,980 B2 | 1/2011 | Sonnenschein et al. | |
| 7,918,845 B2 | 4/2011 | Saadat et al. | |
| 7,918,861 B2 | 4/2011 | Brock et al. | |
| 7,927,327 B2 | 4/2011 | Lu et al. | |
| 7,935,052 B2 | 5/2011 | Dumbauld | |
| 7,942,887 B2 | 5/2011 | Kraemer et al. | |
| 7,955,340 B2 | 6/2011 | Michlitsch et al. | |
| 7,963,976 B2 | 6/2011 | Goldfarb et al. | |
| 7,976,559 B2 | 7/2011 | Goldfarb et al. | |
| 2001/0029317 A1 | 10/2001 | Hayakawa | |
| 2002/0032370 A1 | 3/2002 | Kamata et al. | |
| 2002/0032371 A1 | 3/2002 | Torii | |
| 2002/0123665 A1 | 9/2002 | Miller | |
| 2002/0193663 A1 | 12/2002 | Masuura | |
| 2003/0023142 A1 | 1/2003 | Grabover et al. | |
| 2003/0083550 A1 | 5/2003 | Miyagi | |
| 2003/0236549 A1* | 12/2003 | Bonadio et al. | 606/205 |
| 2004/0044270 A1 | 3/2004 | Barry | |
| 2004/0138525 A1* | 7/2004 | Saadat et al. | 600/104 |
| 2004/0143161 A1 | 7/2004 | Baror et al. | |
| 2004/0193013 A1 | 9/2004 | Iwasaka et al. | |
| 2005/0067460 A1* | 3/2005 | Milliman et al. | 227/180.1 |
| 2005/0272978 A1 | 12/2005 | Brunnen et al. | |
| 2006/0111614 A1 | 5/2006 | Saadat et al. | |
| 2006/0178562 A1 | 8/2006 | Saadat et al. | |
| 2007/0161860 A1 | 7/2007 | Hosoi et al. | |
| 2007/0225556 A1 | 9/2007 | Ortiz et al. | |
| 2007/0225563 A1 | 9/2007 | Ogino | |
| 2007/0225565 A1 | 9/2007 | Ogino | |
| 2008/0132761 A1 | 6/2008 | Sonnenschein et al. | |
| 2008/0139886 A1 | 6/2008 | Tatsuyama | |
| 2008/0221393 A1 | 9/2008 | Padget et al. | |
| 2009/0177041 A1 | 7/2009 | Stefanchik et al. | |
| 2009/0234190 A1 | 9/2009 | Sugisawa | |
| 2009/0270676 A1 | 10/2009 | Sicvol | |
| 2010/0041945 A1 | 2/2010 | Isbell, Jr. | |
| 2010/0056868 A1 | 3/2010 | Kitagawa | |
| 2010/0076266 A1 | 3/2010 | Boulais et al. | |
| 2010/0113879 A1 | 5/2010 | Fukunaga | |
| 2011/0009699 A1 | 1/2011 | Slenker et al. | |
| 2011/0034772 A1 | 2/2011 | Konstorum | |

| | | | | | | |
|---|---|---|---|---|---|---|
| 2011/0071356 A1 | 3/2011 | Edwards | | EP | 2335558 | 6/2011 |
| 2011/0082337 A1 | 4/2011 | Boulais | | WO | WO97/38632 | 10/1997 |
| 2011/0184242 A1 | 7/2011 | Heijmans et al. | | WO | WO2004/043242 | 5/2004 |
| | | | | WO | WO2004/064600 | 8/2004 |

FOREIGN PATENT DOCUMENTS

| | | | | | |
|---|---|---|---|---|---|
| EP | 1849422 | 10/2007 | WO | WO2004/105578 | 12/2004 |
| EP | 1749480 | 12/2008 | WO | WO2006/057700 | 6/2006 |
| EP | 1558124 | 3/2009 | WO | WO2008/146497 | 12/2008 |
| EP | 1849400 | 7/2009 | WO | WO2009/088690 | 7/2009 |
| EP | 2184003 | 5/2010 | WO | WO2009/131912 | 10/2009 |
| EP | 1833356 | 7/2010 | WO | WO2011/018717 | 2/2011 |
| EP | 2100548 | 12/2010 | WO | WO2011/037664 | 3/2011 |
| EP | 2289436 | 3/2011 | | | |

* cited by examiner

FLEXIBLE LAPAROSCOPIC DEVICE

BACKGROUND

1. Technical Field

The present invention relates to laparoscopic devices and, more particularly, to a flexible laparoscopic device having modular parts.

2. Description of the Related Art

Laparoscopy is a surgical procedure that involves making a small incision, e.g., in a person's abdomen, and performing an operation using tools inserted through said insertion. To accomplish such surgeries, surgeons use a variety of laparoscopic tools that are designed to provide visual feedback and allow for the manipulation of internal tissues. However, existing laparoscopic manipulators suffer from certain disadvantages.

In particular, laparoscopic manipulators are designed to allow a certain degree of maneuverability once inside a body cavity. To accomplish this, many existing devices use a system of wires and joints, allowing a surgeon to change the shape of the manipulator during an operation. However, these wires are delicate and their use involves a large number of moving parts, such that there is a significant chance of failure during use. Furthermore, such devices are often single-use, where parts are not interchangeable, and so the entire device must be thrown away after it is used in a surgery if it cannot be adequately sterilized. This leads to substantial waste.

SUMMARY

A laparoscopic device is shown that includes an outer rod having a proximal end connected to an actuating handle and an end distal to said handle, the distal end having an articulated section formed from a plurality of links joined with non-diametrical hinges; an actuation rod disposed within the outer rod, having a proximal end connected to the actuating handle and a distal end connected to a tension element disposed within the articulated section of the outer rod, configured to cause an angular displacement of said articulated section when tension is applied; and an attachment rod disposed within the actuation rod having a proximal end connected to the actuating handle and a distal end having a flexible section and being connected to a tool. The actuating handle includes a tool actuator configured to apply tension to the attachment rod such that the tool is activated; a rod actuator configured to apply tension to the actuation rod such that the articulated section of the outer rod undergoes an angular displacement; and a lockable rotator, configured to rotate the outer rod with respect to the actuating handle.

A laparoscopic device is shown that includes an outer rod having a proximal end connected to an actuating handle and an end distal to said handle, the distal end having an articulated section formed from a plurality of links joined with non-diametrical hinges configured to have a greater angular range in a first direction than in an opposite direction; and an actuation rod disposed within the outer rod, having a proximal end connected to the actuating handle and a distal end connected to a tension element disposed within the articulated section of the outer rod, configured to cause an angular displacement of said articulated section when tension is applied. The actuating handle includes a rod actuator configured to apply tension to the actuation rod such that the articulated section of the outer rod undergoes an angular displacement.

A laparoscopic device is shown that includes an outer rod having a proximal end connected to an actuating handle and an end distal to said handle, the distal end having an articulated section; an actuation rod disposed within the outer rod, having a proximal end connected to the actuating handle, configured to cause an angular displacement of said articulated section when tension is applied; and an attachment rod disposed within the actuation rod having a proximal end connected to the actuating handle and a distal end having a flexible section and being connected to a tool. The outer rod, the actuation rod, the attachment rod, and the actuating handle are each separable and removable.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles provide a modular design using tensioned rods. As compared to existing wire-based designs, the present principles provide a laparoscopic device that has a longer effective life by having fewer points of potential failure and by allowing for the replacement of individual parts that have become dirty or worn out.

Figure 1:
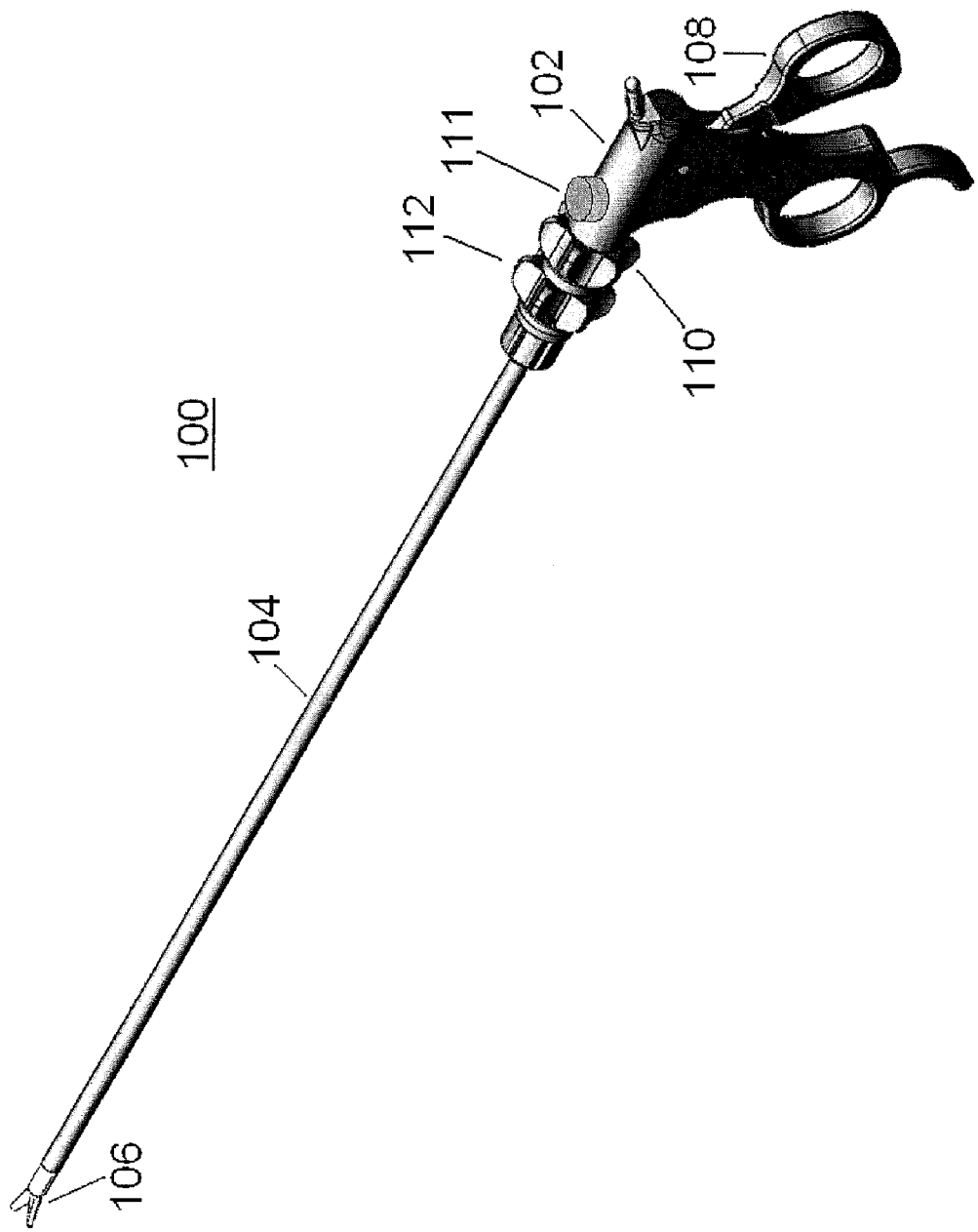
FIG. 1 is a diagram of an exemplary laparoscopic manipulator according to the present principles.

Referring now to the drawings in which like numerals represent the same or similar elements and initially to FIG. 1, a laparoscopic manipulator 100 according to the present principles is illustrated. An actuator handle 102 connects to the proximal end of a rod 104, the rod having a tool portion 106 extending from its distal end. The handle 102 includes an actuating grip 108 that allows the tool portion 106 to be used. Exemplary tools 106 include, e.g., a claw or pincer device configured to grasp and a scissors or other cutting device. The handle 102 further includes a lockable rotator 110 that rotates the rod 104 and tool 106 portions with respect to the actuating handle 102. The lockable rotator 110 may be locked using locking knob 111. Locking knob may be a threaded screw that prevents the rod 104 from rotating, or may be any other suitable device for mechanically preventing rotation. The handle 102 further includes an articulation actuator 112 that causes the distal end of the rod to undergo an angular displacement. The present principles thereby allow a surgeon to achieve three degrees of freedom: one from the angular displacement of the rod, one from the rotation of the rod relative to the handle, and one from the insertion/removal of the rod from the body cavity.

Figure 2:
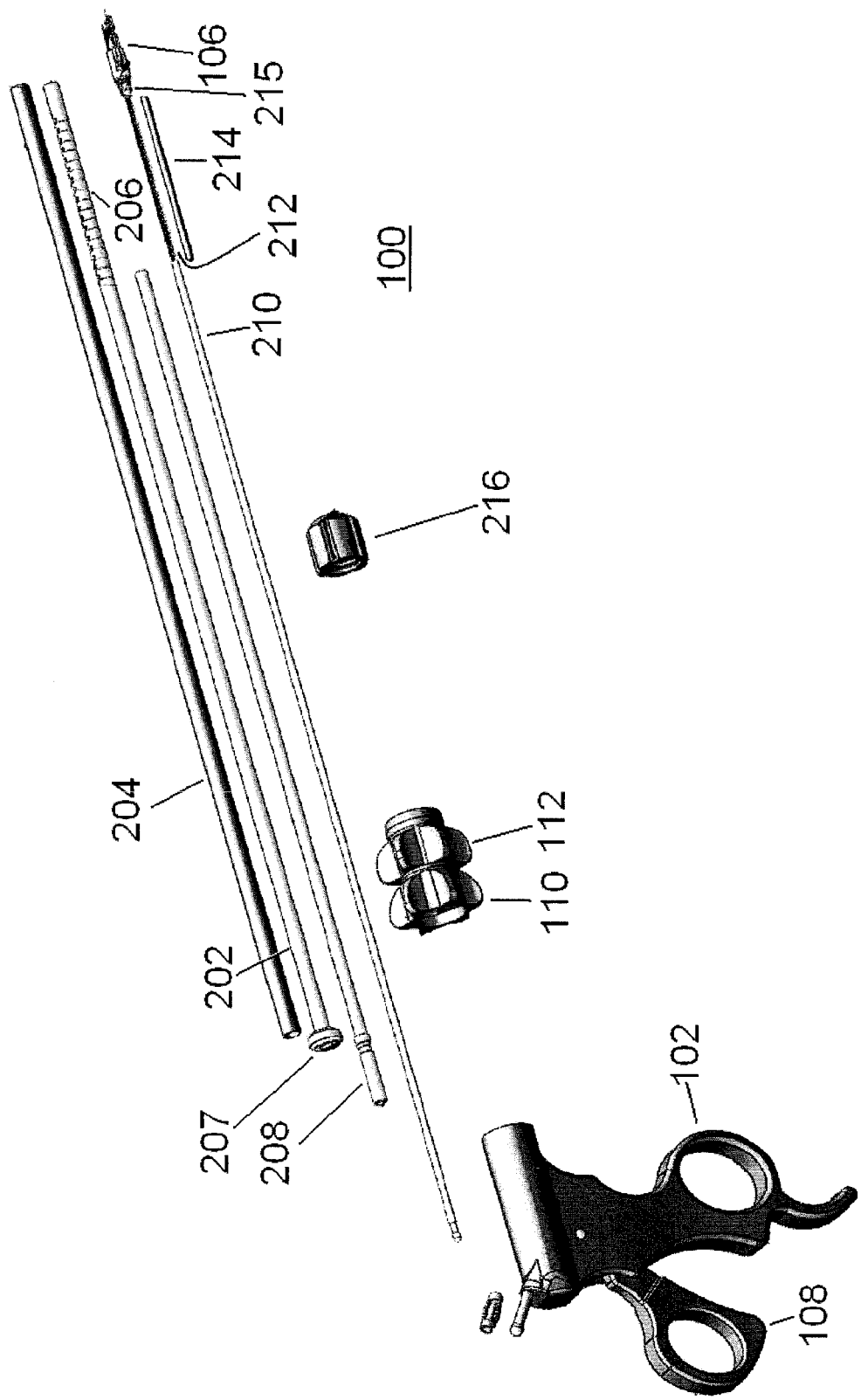
FIG. 2 is an exploded diagram of an exemplary laparoscopic manipulator according to the present principles.

Referring now to FIG. 2, an exploded diagram of the laparoscopic manipulator 100 is shown. An outer rod 202 is shown that has an optional coating 204 and an articulated section 206 at the distal end. The proximal end of the outer rod 202 may have a flanged portion 207 that provides an attachment point between the outer rod and the handle 102. The outer rod 202 may be formed from, for example, stainless steel such as 304 medical-grade steel, or another appropriate material. Inside the outer rod 202 is an actuator rod 208. Actuator rod may also be formed from medical-grade stainless steel or other appropriate material. The coating 204 is, for example, a thin heat-shrink material such as polyester or Teflon®, but it is contemplated that any appropriate, biologically neutral material may be employed. The actuator rod 208 connects to a tension element inside the articulated section 206. When tension is applied to the actuator rod 208, the articulated section 206 deforms and produces an angular displacement. The limits of the angular displacement are controlled by the structure of the articulated section 206, as described below.

An attachment rod 210 passes inside the actuator rod 208 and the outer rod 202 and may be formed from medical-grade stainless steel or other appropriate material. The proximal end of the attachment rod 210 extends into the handle 102 and connects to the actuating grip 108. The distal end of the attachment rod 210 has a flexible portion 212 with an optional coating 214. As above, the coating 214 may be an appropriate heat-shrink material applied so as to form a thin, flexible, and durable covering to prevent wear. The flexible portion 212 may be, for example, a braided stainless steel wire or any other durable material that can withstand bending and tension. The tool portion 106 is attached to the distal end of the flexible portion and has a threaded portion 215 configured to couple with a threaded portion of the outer rod 202 at the end of the articulated section 206. The threading of portion 215 is configured to provide a specific coupling angle with respect to the outer rod 202, such that the tool portion 106 has a specific, fixed rotational orientation relative to the outer rod 202. The rotator 110 and the articulation actuator 112 fit to the handle 102 over the outer rod 202 and are held in place by safety knob 216. The safety knob 216 twists off, allowing the rods 202, 208, and 210 to be detached from the handle 102 and replaced. The safety knob 216 holds the flanged portion 207 of outer rod 202 to the handle 102.

When the actuating grip 108 is moved, the attachment rod 210 moves forward or backward with respect to the outer rod 202. Because the tool portion 106 is fixed to the distal end of the outer rod 202, the movement of the attachment rod 210 with respect to the tool portion causes the tool 106 to activate by, e.g., closing and opening two clamp jaws. When rotator 110 is turned, the entire assembly rotates relative to the handle. This is accomplished by, for example clamping the proximal end of the actuating rod 208 within the rotator 110 and/or the articulation actuator 112. When the articulation actuator 112 is rotated, the actuating rod 208 is moved transversely with respect to the outer rod 202, applying a tension to the rod and thereby to the articulating section 206. This causes the articulating section 206 to bend.

Figure 3:
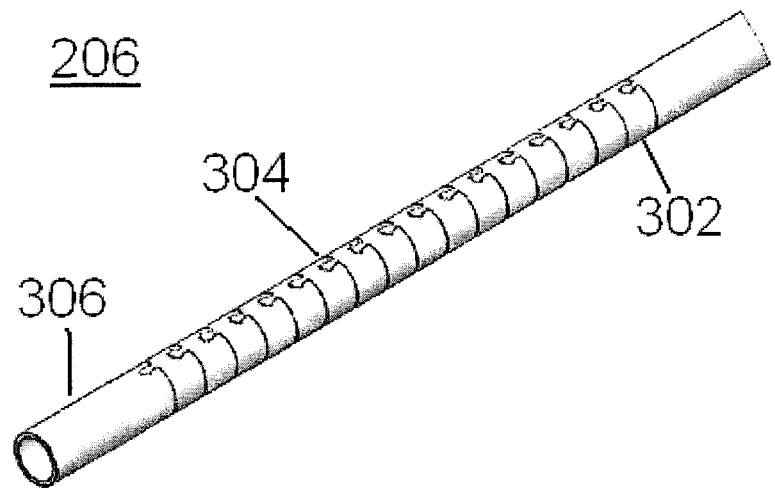
FIG. 3 is a diagram of an articulated rod section according to the present principles.

Referring now to FIG. 3, the articulated section 206 of outer rod 202 is shown in detail. The articulated section is made up of individual links 302, each having a cylindrical cross-section and being attached to the next link by a hinge 304. At the end of the articulated section 206 is a threaded interior 306 that couples to the threaded part of tool portion 106.

Figure 4:
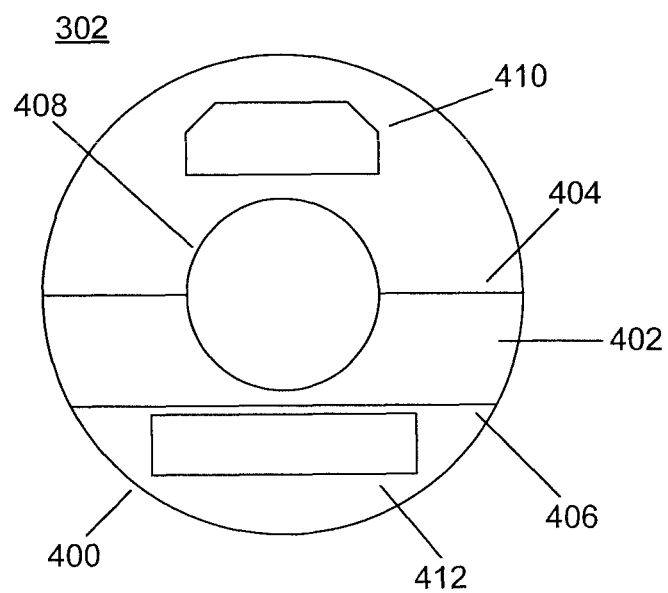
FIG. 4 is a diagram of an individual link of the articulated rod section according to the present principles.

Referring now to FIG. 4, an individual link 302 is shown from a distal perspective. The link 302 is a hollow cylinder 400 having a male coupling portion 402 that has a first side 404 substantially aligned along a radius of the cylinder 400 and a second side 406 that is aligned parallel to the radius of the cylinder. This is one illustrative position of the male coupling portion 402 and should not be construed as limiting—the male coupling portion 402 may be disposed anywhere along the cylinder 400 as long as it is not centrally aligned with a radius of said cylinder 400. The cylinder 400 has a central hole 408, a first spring slot 410, and a second spring slot 412. The central hole 408 accommodates the flexible portion 212 of attachment rod 210, while the two spring slots 410 and 412 accommodate springs formed from, e.g., a memory metal.

Figure 5:
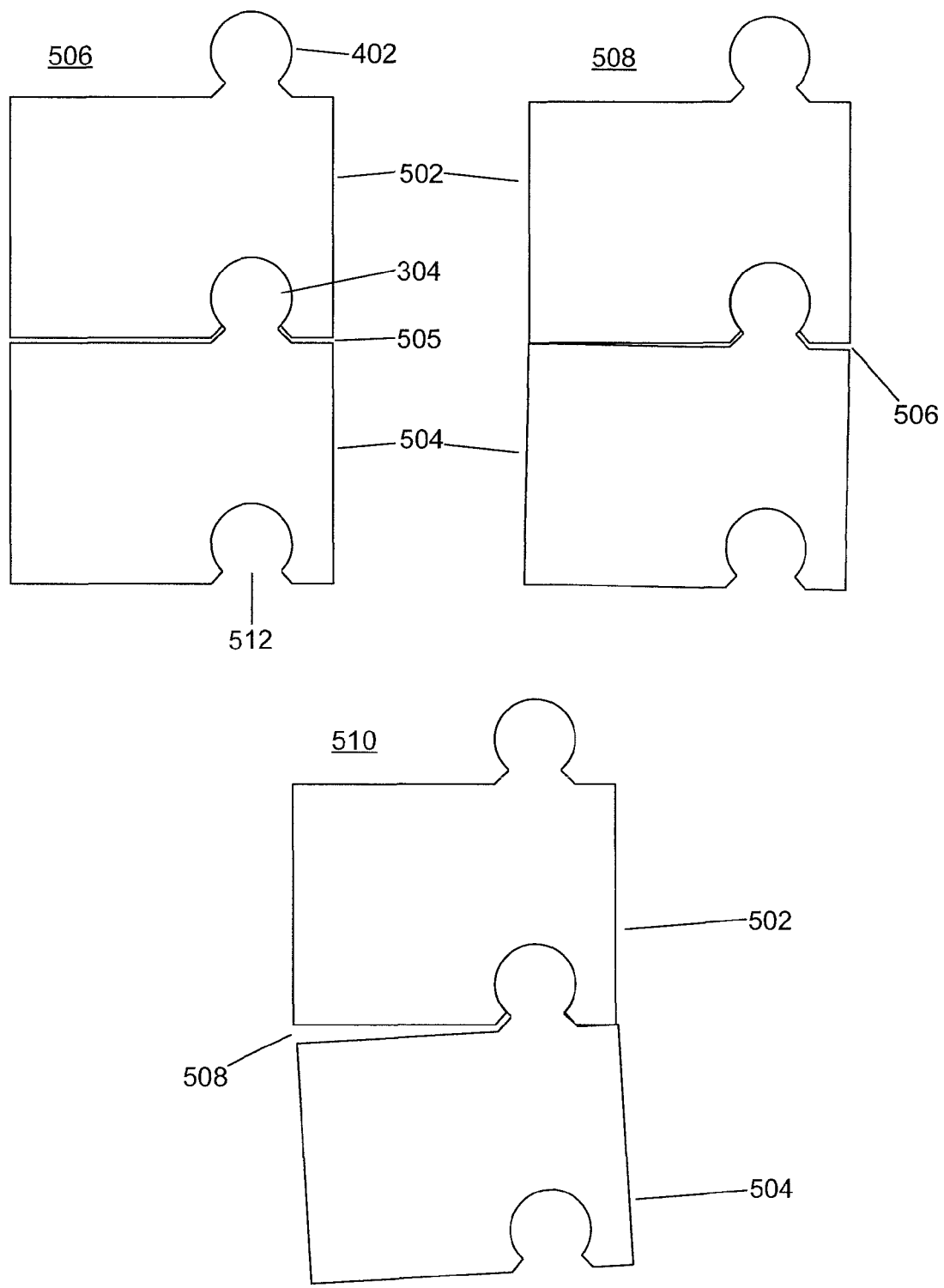
FIG. 5 is a diagram illustrating the articulation of two links.

Referring now to FIG. 5, an exemplary illustration of the bending of two articulated links 302 is shown. A first link 502 is depicted as being joined with a second link 504 in three different positions. In a first position 506, the two links 502 and 504 have zero angular displacement with respect to one another. A small gap 505 exists between the two links 502 and 504. This small gap 505 allows a small amount of movement. It should be noted that, in the depiction of FIG. 5, the male coupling portion 402 lines up with a female coupling portion 512, depicting their non-diametrical arrangement. The male coupling portion 402 of link 504 is disposed within the female coupling portion 512 of link 502, forming a hinge 304.

When the links are in position 508, the small gap 505 is pinched on the long side. Because of the relatively distance between the link edge and the hinge 304, only a small angular displacement 506 is created. Contrast this to the links in position 510. In position 510, there is a much shorter distance between the hinge 304 and the link edges that contact, which results in a much larger angular displacement 508. Thus, by creating a hinge along a non-diametrical axis, articulated links 302 naturally bend in one direction much more than in the other. In this way an articulated structure 206 can be created with unidirectional bending without cutting away portions of the cylinders 400.

Figure 6:
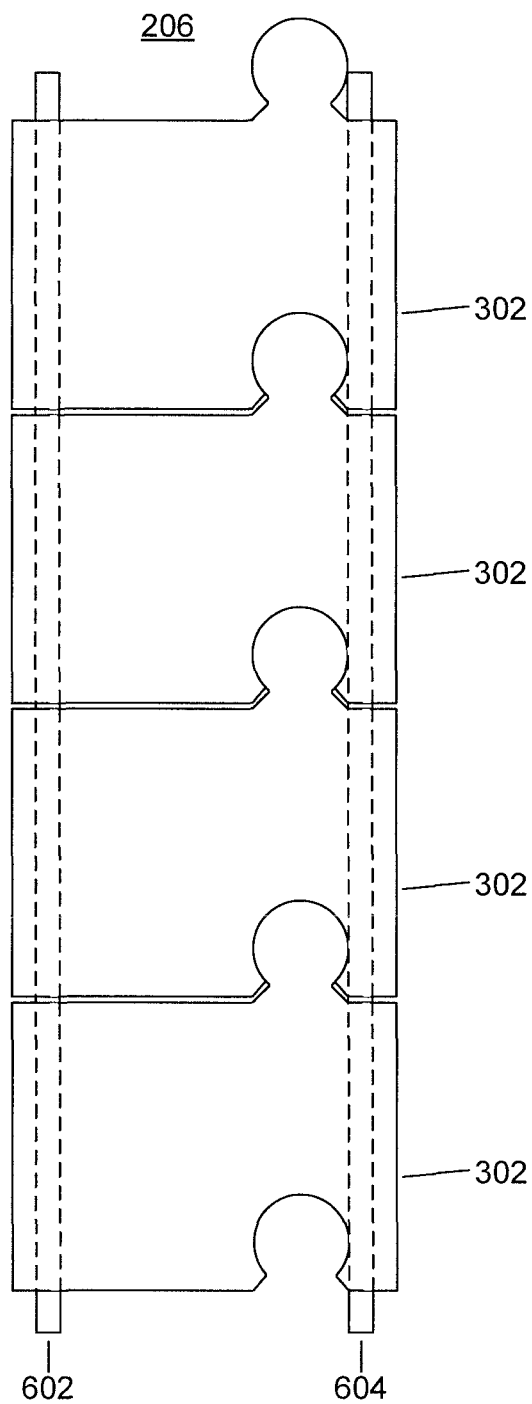
FIG. 6 is a diagram of a length of articulated links with tension elements.

Referring now to FIG. 6, an exemplary illustration of a portion of the flexible portion 206 of attachment rod 210 is shown. A series of coupled links 302 are shown, with spring rods 602 and 604 running through the respective spring holes 410 and 412. Said spring rods 602 and 604 may, for example, be formed from a memory metal such as a nickel-titanium alloy. The spring rods 602 and 604 provide support to the flexible portion 206, preventing disengagement of the links 302 and may be biased in a curved configuration or a straight configuration. A curved bias is advantageous because it permits actuator rod 208 to extend the flexible portion 206 when tension is applied, and permits the spring rods 602 and 604 to return to a curved configuration when tension is released. This avoids a possible malfunction when a tension is applied to a straight spring, effectively applying only a longitudinal force without a transverse (bending) force. An alternative embodiment may comprise only a single spring rod, but the second spring rod lends superior support and reliability.

Having described preferred embodiments of a laparoscopic device (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A laparoscopic device, comprising:
an outer rod having a flanged proximal end connected to an actuating handle and an end distal to said handle, the distal end having an articulated section formed from a plurality of links joined with non-diametrical hinges configured to have a greater angular range in a first direction than in an opposite direction;

an actuation rod disposed within the outer rod, having a proximal end connected to the actuating handle and a distal end connected to a first tension element disposed within the articulated section of the outer rod, configured to cause an angular displacement of said articulated section when tension is applied; and]

an attachment rod disposed within the actuation rod having a proximal end connected to the actuating handle and a distal end having a flexible section and being connected to a tool;

wherein the actuating handle comprises:

a tool actuator configured to apply tension to the attachment rod such that the tool is activated;

a rod actuator configured to apply tension to the actuation rod such that the articulated section of the outer rod undergoes an angular displacement;

a lockable rotator, configured to rotate the outer rod with respect to the actuating handle; and a removable safety knob configured to hold the outer rod, the actuation rod, and the attachment rod to the actuating handle by holding the flanged proximal end of the outer rod to the actuating handle;

wherein the links are cylindrical, having end surfaces perpendicular to a central link axis and parallel to one another.

2. The laparoscopic device of claim 1, wherein the outer rod, the actuation rod, the attachment rod, and the actuating handle are each separable and removable.

3. The laparoscopic device of claim 1, wherein the tool is threaded to couple to the outer rod at a fixed rotational orientation.

4. The laparoscopic device of claim 1, wherein the articulated section comprises a second tension element.

5. The laparoscopic device of claim 1, wherein the first tension element is biased in a curved configuration.

6. The laparoscopic device of claim 1, wherein the first tension element comprises a memory-metal rod.

7. The laparoscopic device of claim 1, wherein the articulated section of the outer rod is configured to undergo unidirectional displacement.

8. The laparoscopic device of claim 1, wherein the outer rod is coated in a bio-inert substance.

9. The laparoscopic device of claim 1, wherein the tool is a grasping device, configured to grasp and release upon actuation of the tool actuator.

10. The laparoscopic device of claim 1, wherein the flexible section of the attachment rod comprises a braided metal wire.

11. The laparoscopic device of claim 1, wherein the actuating handle further comprises a lock configured to immobilize the lockable rotator and prevent the outer rod from moving relative to the handle.

12. The laparoscopic device of claim 1, wherein the links of the articulated section are hollow cylinders comprising a male coupling portion on a face, said male coupling portion being displaced with respect to a diameter of said hollow cylinders.

13. A laparoscopic device, comprising:

an outer rod having a flanged proximal end connected to an actuating handle and an end distal to said handle, the distal end having an articulated section formed from a plurality of links joined with non-diametrical hinges configured to have a greater angular range in a first direction than in an opposite direction; and an actuation rod disposed within the outer rod, having a proximal end connected to the actuating handle and a distal end connected to a tension element disposed within the articulated section of the outer rod, configured to cause an angular displacement of said articulated section when tension is applied;

wherein the actuating handle comprises:

a rod actuator configured to apply tension to the actuation rod such that the articulated section of the outer rod undergoes an angular displacement; and a removable safety knob configured to hold the outer rod and the actuation rod to the actuating handle by holding the flanged proximal end of the outer rod to the actuating handle;

wherein the links are cylindrical, having end surfaces perpendicular to a central link axis and parallel to one another.

14. The laparoscopic device of claim 13, wherein each non-diametrical hinge is formed from a male coupling portion on a first link and a female coupling portion on a second link, said coupling portions being displaced with respect to a diameter of said hinges.

15. The laparoscopic device of claim 14, wherein the coupling portions each have a first side that is aligned with a diameter of the hinges and a second side that is displaced with respect to said diameter.

16. The laparoscopic device of claim 13, wherein the tension element is disposed through the plurality of links such that the links are prevented from displacing transversely with respect to one another.

* * * * *